United States Patent [19]

Breakefield et al.

[11] Patent Number: 5,030,570

[45] Date of Patent: Jul. 9, 1991

[54] DNA ENCODING AND METHOD OF EXPRESSING HUMAN MONOAMINE OXIDASE TYPE A

[75] Inventors: Xandra Breakefield, Newton Center; Yun-Pung Hsu, Lexington, both of Mass.

[73] Assignee: The Eunice Kennedy Shriver Center for Mental Retardation, Waltham, Mass.

[21] Appl. No.: 213,544

[22] Filed: Jun. 30, 1988

[51] Int. Cl.⁵ .................. C12N 15/00; C12N 15/53; C12N 15/63

[52] U.S. Cl. .................. 435/189; 435/320.1; 435/252.3; 435/255; 435/240.2; 536/27

[58] Field of Search .............. 536/27; 435/172, 3, 435/189, 68, 252.33, 320, 69.1, 255, 240.2, 252.3; 935/14

[56] References Cited

PUBLICATIONS

Kwok et al, Nucleotide Sequence of a Full Length cDNA Clone and Amino Acid Sequence of Human Phenylalanine Hydroxylase, Biochemistry 24, 556, 1985.

Wevler et al., 1987, "Comparison of Partial Amino Acid Sequences Deduced from the Nucleotide Sequence of a Bovine Adrenal Monamine Oxidase cDNA Clone to Amino Acid Sequences Obtained from Bovine Liver Monoamine Oxidase Type B," in Flavins and Flavoproteins, Walter de Gruyter & Co., Berlin and N.Y., 725–728.

Weyler et al., Jun. 1987, "Comparison of Partial Amino Acid Sequence of a Bovine Adrenal Monoamine Oxidase cDNA Clone to Amino Acid Sequences Obtained from Bovine Liver Monoamine Oxidase Type B," Flavin Symposium.

Breakefield et al., Nov. 13, 1987, "Molecular Genetic Studies of Monoamine Oxidase", Abstract from Nineteenth Annual Meeting, Am. Soc. Neurochemistry.

Breakefield et al., May 22, 1987, "Gene for A Form of Human Monoamine Oxidase (MAOS) Maps to Xp21-Xp11", Abstract from Am. Soc. Human Genetics.

Hsu et al., May 2, 1988, "Structural Features of Human Monoamine Oxidase A Elucidated from Peptide and cDNA Sequences", Abstract from Soc. for Neuroscience.

Ozelius et al., Aug. 1987, "Gene for A Form of Human Monoamine Oxidase (MAOS) Maps to Xp21-Xp11", Abstract, Conference in Paris.

Titlow et al., May 1988, "*In Vitro* Translation of Monoamine Oxidase (MAO)", FASEB Abstract.

Utterback et al., May 1988, "Monoamine Oxidase Absent in Norrie Disease Patients with Deletion in Chromosomal Region," Soc. for Neuroscience, Abstract.

*Primary Examiner*—Richard A. Schwartz
*Assistant Examiner*—S. L. Nolan
*Attorney, Agent, or Firm*—Fish & Richardson

[57] ABSTRACT

A vector containing DNA encoding human monoamine oxidase type A is disclosed.

12 Claims, 4 Drawing Sheets

Gly-Ser-Phe-Pro-Ser-Val-Trp-Asn-Pro-Ile-Ala-Tyr-Leu-Asp-Tyr-Asn-Asn-Leu

```
                         10          20          30         40          50          60
  1  GAATT CCT GAC ACG CTC GGT CGT AGG AGT GGG GGC CAA AGC ATG AAT CAA
                                                         Met Asn Gln
                         70          80          90        100         110         120
  5      GAG AAG GCG AGT ATC GCG GGC CAC AGG ATG TTC GAC GTA ATC GTG GGA GGC ATT TCA
         Glu Lys Ala Ser Ile Ala Gly His Arg Met Phe Asp Val Ile Val Gly Gly Ile Ser
                                                  ?   ?
                        130         140         150        160         170         180
 25      GGA CTA TCT GCT GCC AAA CTC TTG ACT GAA TAT GGC GTT AGT GTT TTA GAA GCT
         Gly Leu Ser Ala Ala Lys Leu Leu Thr Glu Tyr Gly Val Ser Val Leu Glu Ala
                        190         200         210        220         230         240
 45      CGG GAC AGG GTT GGA AGA ACA TAT ACT ATA AGG AAT GAG CAT GTT GAT TAC GTA GAT
         Arg Asp Arg Val Gly Arg Thr Tyr Thr Ile Arg Asn Glu His Val Asp Tyr Val Asp
                        250         260         270        280         290         300
 65      GTT GGT GGA GCT TAT GGA CCA CAA AAC AGA ATC TTA CGC TTA TCT AAG GAG CTG
         Val Gly Gly Ala Tyr Gly Pro Gln Asn Arg Ile Leu Arg Leu Ser Lys Glu Leu
                        310         320         330        340         350         360
 85      GCC ATA GAG ACT TAC AAA GTG AAT GTC AGT GAG CGT CTC CTC GTT CAA GGG AAA
         Gly Ile Glu Thr Tyr Lys Val Asn Val Ser Glu Arg Leu Leu Val Gln Gly Lys
                        370         380         390        400         410         420
105      ACA TAT CCA TTT CGG GCC TTT CCA CCA GTA TGG AAT CCC ATT GCA TAT TTG GAT TAC
         Thr Tyr Pro Phe Arg Ala Phe Pro Pro Val Trp Asn Pro Ile Ala Tyr Leu Asp Tyr
                        430         440         450        460         470         480
125      AAT AAT CTG TGG AGG ATA GAT AAC ATG AAG ATG GGG ATT CCA GAT GCA CCC TGG
         Asn Asn Leu Trp Arg Ile Asp Asn Met Lys Met Gly Ile Glu Ile Pro Asp Ala Pro Trp
                        490         500         510        520         530         540
145      GAG GCT CAA CAT GCT GAC AAA TGG AAA ATG ACC ATG AAA GAG CTC ATT GAC AAA ATC
         Glu Ala Gln His Ala Asp Lys Trp Lys Met Thr Met Lys Glu Leu Ile Asp Lys Ile
             Ser         Pro Lys
                        550         560         570        580         590         600
165      TGC TGG ACA AAG ACT AGG CGG TAT CTT GTG AAT GTG AAT GTG ACC TCT
         Cys Trp Thr Lys Thr Arg Arg Tyr Leu Phe Val Asn Ile Val Thr Ser
                                   Ala Phe                          Val
```

FIG. 2-2

```
       610            620            630            640            650            660
   GAG CCT CAC GAA GTG TCT GCC CTG TGG TTC TTG TGG TAT GTG AAG CAG TGC GGG GGC ACC
185 Glu Pro His Glu Val Ser Ala Leu Trp Phe Leu Trp Tyr Val Lys Gln Cys Gly Gly Thr 670            680            690            700            710            720
   ACT CGG ATA TTC TCT GTC ACC AAT GGT GGC CAG GAA CGG AAG TTT GTA GGT GGA TCT GGT
205 Thr Arg Ile Phe Ser Val Thr Asn Gly Gly Gln Glu Arg Lys Phe Val Gly Gly Ser Gly
                                                                                Cys
       730            740            750            760            770            780
   CAA GTG AGC GAA CGG ATA ATG GAC CTC CTC GGA GAC CAA GTG AAC CTG AAC CAT CCT GTC
225 Gln Val Ser Glu Arg Ile Met Asp Leu Leu Gly Asp Gln Val Lys Leu Asn His Pro Val
   Asn                    Glu 790            800            810            820            830            840
   ACT CAC GTT GAC CAG AGT GAC ATC ATA GAG ACG CTG AAC CAT GAA CAT CTA TAT
245 Thr His Val Asp Gln Ser Ser Asp Ile Ile Glu Thr Leu Asn His Glu His Gly Tyr 850            860            870            880            890            900
   GAG TGC AAA TAC GTA ATT AAT GCG CCT CCG ACC TTG ACT GCC AAG ATT CAC TTC AGA
265 Glu Cys Lys Tyr Val Ile Asn Ala Pro Pro Thr Leu Thr Ala Lys Ile His Phe Arg 910            920            930            940            950            960
   CCA GAG CTT CCA GCA GAG AAC CAG TTA ATT CAG CGT CTT CCA GGA ATG GCT GTC ATT
285 Pro Glu Leu Pro Ala Glu Asn Gln Leu Ile Gln Arg Leu Pro Gly Met Ala Val Ile 970            980            990           1000           1010           1020
   AAG TGC ATG ATG TAT AAG TAC AAG GAG GCC TTC TGG AAG AAG AAG GAT TAC TGT GGC ATG
305 Lys Cys Met Met Tyr Lys Tyr Lys Glu Ala Phe Trp Lys Lys Lys Asp Tyr Cys Gly Met 1030           1040           1050           1060           1070           1080
   ATC ATT GAA GAT GAA GCT CCA ATT TCA ATA ACC TTG GAT GAC AAG CCA GAT GGG
325 Ile Ile Glu Asp Glu Ala Pro Ile Ser Ile Thr Leu Asp Asp Lys Pro Asp Gly 1090           1100           1110           1120           1130           1140
   ATT CTG CCT GCC ATC ATG GGC TTC ATT CTT GCC CGG AAA GCT GAT CGA CTT GCT AAG CTA
345 Ser Leu Pro Ala Ile Met Gly Phe Ile Leu Ala Arg Lys Ala Asp Arg Leu Ala Lys Leu 1150           1160           1170           1180           1190           1200
   TCA CTG GAA ATA AGG AAG AAA AAG AAA ATC TGT GAG CTC TAT GCC AAA GTG CTG GGA TCC CAA
365 Ser Leu Glu Ile Arg Lys Lys Lys Lys Ile Cys Glu Leu Tyr Ala Lys Val Leu Gly Ser Gln
```

FIG. 2-3

```
                          1210              1220              1230              1240              1250              1260
385  GAA GCT TTA CAT CCA GTG CAT TAT GAA GAG AAG AAC TGG TGT GAG CAG TAC TCT GGG
     Glu Ala Leu His Pro Val His Tyr Glu Glu Lys Asn Trp Cys Glu Gln Tyr Ser Gly
                          1270              1280              1290              1300              1310              1320
405  GGC TGC TAC ACG GCC TAC TTC CCT GGG ATC ATG ACT CAA TAT GGA AGG GTG ATT CGT
     Gly Cys Tyr Thr Ala Tyr Phe Pro Gly Ile Met Thr Gln Tyr Gly Arg Val Ile Arg
                          1330              1340              1350              1360              1370              1380
425  CAA CCC GTG GGC AGG ATT TTC TTT GCG GGC ACA GAG ACT GCC ACA AAG TGG AGC TAC
     Gln Pro Val Gly Arg Ile Phe Phe Ala Gly Thr Glu Thr Ala Thr Lys Trp Ser Tyr
                          1390              1400              1410              1420              1430              1440
445  ATG GAA GGG GCA GTT GAG GCT GGA CGA GCA GCT AGG GAG GTC TTA AAT GGT CTC GGG
     Met Glu Gly Ala Val Glu Ala Gly Arg Ala Ala Arg Glu Val Leu Asn Gly Leu Gly
                          1450              1460              1470              1480              1490              1500
465  AAG GTG ACC GAG AAA GAC ATC TGG GTA CAA GAA CCT GAA TCA AAG GAC GTT CCA GTA
     Lys Val Thr Glu Lys Asp Ile Trp Val Gln Glu Pro Glu Ser Lys Asp Val Pro Val
                          1510              1520              1530              1540              1550              1560
485  GAA ATC ACC CAC ACC TTC TGG GAA AGG AAC CTG CCC TCT CTT GGC CTG CTG AAG ATC
     Glu Ile Thr His Thr Phe Trp Glu Arg Asn Leu Pro Ser Leu Gly Leu Leu Lys Ile
                          1570              1580              1590              1600              1610              1620
505  ATT GGA TTT TCC ACA GTA ACT GCC CTG GGG TTT GTG CTG TAC AAA TAC AAG CTC CTG
     Ile Gly Phe Ser Thr Val Thr Ala Leu Gly Phe Val Leu Tyr Lys Tyr Lys Leu Leu
                          1630              1640              1650              1660              1670              1680
525  CCA CGG TCT TGA AGT TCT GTT TCT CTT ATG CTC TGG TTT TCA ATA CCA AGA
     Pro Arg Ser
                          1690              1700              1710              1720              1730              1740
     GGA AAA TAT TGA CAA GTT TAA AGG CTG TGT CAT TGG GCC ATG TTT AAG TGT ACT TTT
                          1750              1760              1770              1780              1790              1800
     AAC TAC CTT TGG CTT AAT TCC AAT TGT TAA AGT AAA AAC AAT TCA AAG AAT CAC CTA
                          1810              1820              1830              1840              1850              1860
     ATT AAT TTC AGT AAG ATC AAG CTC CAT CTT ATT TGT CAG TGT AGA TCA ACT CAT GTT AAT
                          1870              1880              1890              1900              1910              1920
     TGA TAG AAT AAA GCC TTG TGA TCA CTT TCT GAA ATT CAC ACT CAT AAA GTT AAA CGT GAT GTG CTC
                          1930              1940              1950              1960
     ATC AGA AAC AAA AAA AAA AAA AAA AAG GAA TTC
```

DNA ENCODING AND METHOD OF EXPRESSING HUMAN MONOAMINE OXIDASE TYPE A

This invention was made with Government support under NS 21921 awarded by NIH. The Government has certain rights in the invention.

BACKGROUND OF THE INVENTION

This invention relates to human monoamine oxidase A and to recombinant DNA techniques.

Monoamine oxidase (monamine: $O_2$ oxidoreductase, EC 1.4.3.4.; MAO) catalyzes the oxidative deamination of a wide variety of dietary amines and neurotransmitters such as dopamine, norepinephrine, and serotonin. It is an integral protein of the outer mitochondrial membrane and is present in all types of cells. Two isoenzymic forms (Types A and B) have been identified and are believed to consist of similar but non-identical proteins.

MAO has been implicated in a number of neurophysiological disease states, and MAO inhibitors have been used as antidepressants. MAO-B metabolizes the neurotoxin 1-methyl-4-phenyl-1,2,3,6-tetrahydropyridine (MPTP) to an active form which elicits Parkinsonian symptoms (Markey et al., 1984). Lower than normal levels of MAO activity have also been described in patients with various psychiatric disorders.

Human MAO-A and MAO-B are probably encoded by separate genes, which are closely linked on the X chromosome. A submicroscopic deletion in the Xp11.3 region of the human X chromosome results in the loss of both MAO-A and MAO-B activity in humans.

SUMMARY OF THE INVENTION

In general, the invention features a vector containing DNA encoding mature human monoamine oxidase A (MAO-A). As will be apparent from the detailed description below, "mature human monoamine oxidase A" refers to the biologically active MAO-A molecule; thus the term as used herein is broad enough to include a DNA sequence (genomic or, more preferably, cDNA) which encodes at least the mature human MAO-A, and which can also encode human or other (e.g., bovine, yeast, or bacterial) leader sequences, or hybrid leader sequences.

Preferably, for expression of the MAO-A polypeptide in *E. coli*, DNA encoding MAO-A is under the control of regulatory DNA, which consists of a promoter and a signal peptide encoding sequence; most preferably, the lac promoter and OmpA, phoA, or pelB signal sequence. For expression in yeast, MAO-A DNA is under the control of the MFα1 promoter and signal sequence. For expression in mammalian cells, MAO-A DNA is under the control of the viral long terminal repeat (LTR) sequence.

MAO-A DNA can be used therapeutically and diagnostically for diseases involving the MAO-A and MAO-B gene products; e.g., the MAO-A gene is a candidate gene for mental retardation and illness, thus the DNA or RNA can be used diagnostically as a probe to detect MAO-A gene alterations or point mutations or to detect altered levels of MAO RNA that may be associated with manic depression or psychotic states, including those requiring treatment with MAO inhibitors. The MAO-A gene can also be used therapeutically in gene therapy to correct MAO deficiencies.

The vectors of the invention are used to transform *E. coli* cells, yeast cells, preferably the yeast cells are *Saccharomyces cerevisiae*, or to transfect mammalian cells, e.g., NIH3T3 or BHK21 cells, to produce biologically active human MAO-A. The MAO-A polypeptide can be used therapeutically to develop MAO inhibitors that are useful for treatment of psychotic disorders, or to metabolize monoamines released during digestion of certain foods which, in patients in which monoamino oxidase is inhibited by drugs, act as false transmitters. In addition, purified recombinant MAO-A can also be used to treat MAO-deficient individuals. MAO-A can also be used diagnostically to make monoclonal antibodies which are useful for assessing altered MAO enzyme levels associated with human diseases.

Other features and advantages of the invention will be apparent from the following description of the preferred embodiments thereof, and from the claims.

The drawings will first briefly be described.

DRAWINGS

FIG. 1 is a peptide whose deduced DNA sequence was used to made a synthetic 47-mer probe.

FIG. 2 is the complete nucleotide sequence and corresponding amino acid sequence of the human MAO-A cDNA, HM11.

DESCRIPTION OF THE PREFERRED EMBODIMENTS

GENERAL APPROACH FOR CLONING MAO-A GENES

The human MAO-A cDNA was isolated from human liver cDNA and human placental cDNA libraries, and then the cDNA was used to isolate the genomic MAO-A gene from a human genomic cosmid library. The strategy for obtaining the genomic and cDNA sequences for human MAO-A was as follows. First, a bovine MAO-B peptide fragment would be purified and sequenced, and that sequence used to make a probe for a bovine cDNA library, from which a bovine cDNA would be obtained; the bovine cDNA in turn would be used to screen a human cDNA library, and the resulting human cDNA used to obtain the human qenomic sequence.

Isolation of Bovine MAO cDNA

The isolation of a bovine MAO cDNA clone, G1, was carried out by John Powell, using amino acid sequence information derived from a purified fragment of bovine MAO-B, designated XOB3. FIG. 1 gives the amino acid sequence of the XOB3 peptide, from which the DNA sequence of a synthetic 47-mer bovine MAO-B oligonucleotide was deduced. The 47-mer oligonucleotide was synthesized using an Applied Biosystems 380A synthesizer by the phosphoamidite method and purified by PAGE. 100 ng of the oligonucleotide was labelled with $\gamma[^{32}P]ATP$ (7000 Ci/mMol, NEN, Boston, Mass.) usinq T4-polynucleotide kinase (Boehringer Mannheim, Indianapolis, Ind.). The oligonucleotide was synthesized without degenerations using the most common code usage for the appropriate amino acids (Grantham et al., 1980, Nucleic Acids Res. 8: 49). The 47-mer was then used as a probe to screen a bovine cDNA library.

A cDNA library was constructed using bovine adrenal medulla RNA and then screened with the 47-mer oligonucleotide probe to find a bovine MAO clone.

Poly(A)+RNA was isolated from bovine adrenal medulla and purified according to the method of LoMedico and Saunders (1976, Nucleic Acids Res. 3: 381). A cDNA library was constructed in pBR322 according to the method of Gubler and Hoffman (1983, Gene 25: 263). A total of approximately 14,000 different colonies were screened. Each of 7000 colonies was transferred to a 20×20 cm nitrocellulose filter and lysed according to the method of Grunstein and Hogness (1975, Proc. Nat. Aca. Sci. 72: 3961), and the filters were prehybridised at 37° C. for 4h in hybridisation buffer (6×SSC; 5×Denhardt; 50 mM sodium phosphate, pH 6.5; 100 μg/ml boiled herring DNA: 20% (v/v) deionised formamide; 0.1 g/ml dextran sulphate, mol. wt. 500,000). The filters were then hybridised at 37° C. for 12 h with the oligonucleotide (100,000 cpm/ml) in hybridization buffer. The nitrocellulose filters were washed at 37° C. for 30 min in 1×SSC/0.1% SDS with several changes of buffer and exposed overnight with an intensifying screen at −70° C. Positive colonies were picked and rescreened under the same conditions.

A single strongly hybridizing clone (G1) from a field of 14,000 cDNA clones was obtained and digestion of the plasmid DNA with the restriction enzyme PstI revealed a 500 nucleotide insert. Bovine and human MAO have approximate molecular weights of 59,650 daltons, corresponding to about 527 amino acids or an expected DNA coding length of 1581 nucleotides. Thus, the bovine G1 clone did not encode the entire bovine MAO protein.

To obtain a longer bovine MAO clone, the G1 clone was transcribed into RNA, which was used as a probe to search another bovine adrenal medulla cDNA library (obtained from Icangelo et al., 1986, Nature 323:82, and screened according to Maniatis et al, 1982, Molecular Cloning: A Laboratory Manual, Cold Spring Harbor, N.Y.). The 500 kb G1 insert was transferred into the PstI site of the pGEM2 vector (Promega Biotec, Madison, Wis.), downstream from the SP6 phage promoter, and the recombinant plasmid was used as a template for transcription from the SP6 promoter of an RNA probe complementary to the insert.

Hybridization of the RNA probe to the larger bovine cDNA library was performed in a solution containing 20% formamide, 6×SSC, 5×Denhardt's solution, 0.1% SDS, 0.2 mg/ml denatured salmon sperm DNA, 0.2 mg/ml yeast tRNA, 1 mM EDTA. Incubation was done at 50° C. for 48 h. The filters were washed in 233 SSC/0.1% SDS three times, 10 min. each, at room temperature, and then washed in 0.5×SSC/0.1% SDS at 50° C. twice, for 30 min. each.

A total of 8 positives, obtained from a library of 200,000 colonies, contained either a 2.7 kb or a 1.2 kb insert. Restriction mapping showed that the 1.2 kb clones were a subset of the 2.7 kb clones. One of the 2.7 kb clones, 34-3A, was used for futher study.

Restriction fragments from the bovine clones G1 and 34-3A were subcloned into M13mp18 and M13mp19, and DNA sequences determined by the dideoxy method using $^{35}$S-labelled dATP (Williams et al., 1986, Biotechniques 4:138; Reed et al., 1986, Biotechniques 4:306). Exonuclease III treatment, as described by Henikof et al., 1984, Gene 28:351, was used to generate further clones for sequence analysis. The region of the 0.5 kb insert complementary to the 47-mer oligonucleotide probe coded for a protein sequence identical to that of the corresponding bovine liver MAO peptide except for three mismatches. Comparison of the predicted amino acid sequence from these two bovine MAO clones with that obtained from protein sequences of tryptic peptides of bovine liver MAO-B showed an overall homology of 73%. This suggested that, although the G1 and 34-3A clones were identified using an oligonucleotide probe deduced from an MAO-B peptide sequence, the isolated cDNA clones are MAO-A clones.

Isolation of Human MAO-A cDNA

In order to isolate a human MAO-A cDNA clone, a human liver cDNA library (Kwok et al., 1985, Biochem. 24: 556) and a human placental cDNA library were screened using the 34-3A bovine MAO cDNA clone as a probe. Human liver expresses both MAO-A and MAO-B, while placenta expresses only MAO-A. One positive clone, HM11, containing a 2.0 kilobase (kb) insert was obtained from the human liver library and four positive clones containing inserts of 2.8 kb, 2.5 kb, 0.5 kb and 0.2 kb from the human placenta library were identified using the bovine cDNA probe. The inserts from these positive clones were subcloned into the vector M13mp18 and sequenced by the dideoxy method (Williams et al., supra; Reed et al., supra). To facilitate sequencing of the liver cDNA clone, directional deletions were made and regions of ambiguity were resolved using synthetic site-specific primers.

The complete sequence of the 2.0 kb cDNA from human liver, HM11, is given in FIG. 2. It contains an open reading frame of 527 amino acids which starts with an ATG at nucleotide 51 and stops with a TGA at nucleotide 1632. When 156 out of 161 amino acids of the deduced protein are compared with the proteolytic peptides from human placenta MAO-A, 97% of the amino acids are identical (underlined). Further evidence that HM11 is a MAO-A clone was provided by partial sequencing of the four cDNA clones from human placenta: there is greater than 99% homology between HM11 and the human placenta clones in the 1.2 kb region that was compared. And, in the positions where there are mismatches between HM11 and the MAO-A peptides (Asp-150, Asp-153, Gly-224, Gln-225 and Met-231), the two longer placenta clones and the HM11 liver clone contain identical amino acids. Therefore, it is highly unlikely that these mismatches arose from DNA cloning and sequencing artifacts, but may be explained by the presence of DNA polymorphisms or heterogeneous MAO-A subunits.

The HM11 liver clone contains nucleotides involved in translation initiation that are identical to the consensus sequence for the optimal initiation of translation in higher eukaryotes (Kozak, 1986, Cell 44: 283): two nucleotides around the first ATG of Hm11, an A located three bases upstream (nucleotide 48 in FIG. 2), and a G immediately downstream (nucleotide 54). The nucleotide sequence of HM11 is about 88% homologous to the bovine MAO-A cDNA throughout the entire coding region. In contrast, sequences upstream from the first ATG are quite divergent; only 11 out of 26 nucleotides matched. This is consistent with the presence of a 5' untranslated region. The first in-frame stop codon of HM11 is followed about 60 nucleotides downstream by two more stop codons, TGA and TAA. A string of A's appears in the 3' end, preceded by the polyadenylation signal AATAAA around position 1870. The estimated molecular weight of the deduced protein, 59,677, agrees with values determined biochemically (Cawthon et al., 1981, Neurochem. 37: 363).

These features indicate that HM11 contains the entire coding region for MAO-A. (*E. coli* cells containing HM11 have been deposited with the American Type Culture Collection, and assigned Accession Number 67740.)

Isolation of Human MAO-A Genomic DNA

A genomic clone (A2) encoding MAO-A was isolated from a human genomic cosmid library using the MAO-A-encoding insert from HM11 as a probe. The library was constructed from human genomic DNA inserted into the cosmid vector C2XB (Bates et al., 1983, Gene 26: 137; Bates et al., 1987, Methods Enzymol. 153: 82). The A2 clone contains a genomic DNA insert of approximately 30 kb, within which are located the exons that together encode MAO-A. (*E. coli* cells containing A2 have been deposited with the American Type Culture Collection, and assigned Accession Number 67741.)

Expression of Human MAO in E. coli

The human MAO-A gene can be expressed and secreted in bacterial host cells, preferably *E. coli*, using vectors based on the pUC family of plasmids (Yanisch-Perron et al., 1985, Gene 33: 103). These plasmids contain the lac promoter-operator (lac P/O), which is inducible by isopropyl-β-D-thiogalactoside (IPTG) (Yanisch-Perron et al., supra). For directing the membrane translocation of the processed protein into the periplasmic space of *E. coli* or secretion into the culture medium, leader sequences of the following genes can be used: (1) the outermembrane protein A (ompA) (Movva et al., 1980, J. Biol. Chem. 255: 27), (2) the alkaline phosphatase (phoA) (Inouye et al., 1982, J. Bact., 149: 434), or (3) the pectate lyase (pelB) (Lei et al., 1987, J. Bact. 169: 4379). The MAO-A coding region from the cDNA clone, HM11, can be precisely fused to DNA fragments encoding the signal sequence according to standard DNA methods. A ribosomal binding site will precede the coding region to direct efficient translation initiation. Ligated DNA can be transformed into *E. coli* according to conventional techniques and transformants containing the recombinant plasmids can be verified by restriction enzyme analysis. Human MAO-A polypeptide can then be produced by the plasmid-bearing strain and purified from the culture medium or the cell lysates. If the human MAO-A polypeptide is found to be degraded by *E. coli* proteolytic enzymes, efficient expression of the polypeptide can be achieved by designing a small protective "cap" in the form of a protease-resistant amino acid leader sequence, as described by Sung et al., 1987, Methods in Enzymology 153: 385.

Expression of Human MAO-A in Yeast

The MAO-A gene can be expressed in yeast using the yeast secretion vector paC3, which consists of a 1.7 kb yeast genomic fragment containing the MFα1 structural gene, as well as its promoter and transcription termination sequences in a pBR322-based vector (Zsebo et al., 1986, J. Biol. Chem. 261: 5858). A restriction fragment from HM11 encoding MAO-A (the ends may be modified if necessary with appropriate adaptor or linker sequences (New England Biolabs, Beverly, Mass.)) can be inserted in place of the HindIII-SalI fragment of paC3 downstream of the α-factor encoding fragment so that a Lys-Arg dipeptide lies immediately upstream of the first codon of MAO-A. The Lys-Arg unit forms a recognition site for the KR endoprotease and is introduced so that the α-factor sequence can be cleaved off the hybrid protein between the α-factor peptide and human MAO-A. The BamHI yeast fragment, containing the MFα1 sequence fused to the MAO-A gene, must then be transferred to a yeast-based vector, such as the pYE vector which contains a unique BamHI site, for expression in yeast. After transformation of the recombinant DNA into yeast, preferably of the species *Saccharomyces cerevisiae*, the transformants ca be cultured under appropriate conditions to produce a MFα1-human MAO-A fusion peptide. The encoded product will contain the first 83 amino acids of the native α-factor precursor, which includes a signal peptide sequence for secretion of the fusion polypeptide in yeast. This fusion polypeptide contains the KR endoprotease recognition sequence and, therefore, the 83 amino acid precursor will be processed from the MAO-A polypeptide naturally in the cell. The COOH terminus does not require proteolytic processing for maturation, as a translation termination codon is present at the end of the MAO-A gene.

Expression of Human MAO-A in Mammalian Cells

Human MAO-A can be produced in mammalian cells, e.q., NIH3T3 or BHK21 cells, using a suitable mammalian cell vector, such as the retroviral shuttle vector pZIP-NeoSVX (Cepko et al., 1984, Cell 37: 1053). In addition, a metallotheionein promoter (Choo et al , 1986, DNA 5: 529) can also be inserted upstream of the MAO-A gene to allow inducibility of MAO-A expression.

A MAO-A-encoding restriction fragment from the HM11 clone can be inserted at the BamHI site downstream from the long terminal repeat (LTR) of the SVX vector by use of the appropriate adapter sequence. For example, the human MAO-A gene can be removed from the HM11 clone and inserted into SVX by first digesting with the restriction enzymes EcoRI and DraI and isolating the MAO-A encoding fragment. The EcoRI-DraI ends of the fragment can then be converted to BamHI ends using DraI/BamHI adaptors and the BamHI MAO-A insert is ligated to BamHI-digested SVX. (Any other suitable restriction sites in the HM11 clone or the SVX vector can be used.) The ligated DNA can be transformed into *E. coli*, since the SVX vector can shuttle between *E. coli* and mammalian cells, for selection of the MAO-A-SVX recombinant clone, and then transfected into NIH3T3 or BHK21 cells. NIH3T3 cells, maintained in Dulbecco's Modified Eagle's Medium supplemented with 10% calf serum, can be transfected with the MAO-A-SVX shuttle vector using the calcium-phosphate technique of Graham and van der Eb, as modified by Parker and Stark (1979, J. Virol. 31: 360). Similarly, BHK21 cells can be transfected using the calcium-phosphate method of Wigler et al. (1978, Cell 14: 725) and selecting for G418 resistance in GIBCO medium.

Purification of MAO-A Proteins

Recombinant MAO-A expressed in the systems described above can be purified from cellular supernatants according to the procedures of Weyler and Salach (1985, J. Biol. Chem. 260: 13199).

Diagnostic and Therapeutic Use

The human MAO-A gene or its complementary RNA may be used to diagnose or treat medical disorders involving the MAO-A and MAO-B genes and gene products. For example, alterations in the human MAO-A gene may cause changes in gene expression or production of an altered protein resulting in disorders such as mental retardation, manic depression, or psychoses; such alterations, for example, rearrangements, point mutations, or regulatory mutations that result in altered levels of the MAO-A RNA, may be detected using MAO-A DNA or RNA diagnostically. A description of three detection systems for gene alterations follows.

MAO-A Probes

MAO-A DNA or RNA can be radioactively labeled and used as a probe in a Southern blot, as described by Maniatis et al., supra, to detect the MAO-A gene in total human DNA. (The MAO-B gene can also be detected using this technique if certain parameters are varied, e.g., hybridization temperature or salt concentration.) To prepare an MAO-A DNA probe, the MAO-A encoding EcoRI fragment of HM11 can be isolated according to conventional procedures and radioactively labeled as described in Maniatis et al., supra. To prepare an MAO-A RNA probe, the MAO-A EcoRI DNA fragment can be inserted into the vector SP6 (obtained from Promega Biotech) and the sense strand of MAO-A DNA can be used as a template for transcription in the presence of radioactive nucleotides.

DNA Blot Analysis

The radioactive DNA or RNA probe can be used to detect the MAO-A gene in total human DNA that has been digested with one or more restriction enzymes; the probe will identify one or more restriction enzyme fragments containing part or all of the MAO-A gene. Gross rearrangements of the MAO-A gene can be detected using restriction enzymes that digest the DNA at two or only a few sites near or within the gene, whereas rearrangements involving smaller regions of the gene are more likely to be detected if restriction enzymes are used that digest the DNA at many sites within or near the gene. Sample human DNA from individuals suspected of having an MAO-associated disorder can be compared to human DNA from healthy individuals and abnormal patterns of digestion can be used as an indication of MAO-linked disorders.

RFLP and Linkage Analysis

Random DNA samples can be screen for single nucleotide differences in MAO-A coding regions and intervening sequences by using different restriction enzymes to digest the DNA sample and separating the resulting restriction fragments on a Southern blot, as described in Maniatis et al., supra. The MAO-A cDNA clone detects a EcoRV RFLP that can be used for studying linkage between the MAO-A locus and disease states. The MAO-A genomic clone can also be used to detect restriction fragment length polymorphisms (RFLPs) in the MAO-A gene, e.g., an MspI RFLP. The A2 genomic clone can be used as a probe after repetitive sequences have been removed. Repetitive sequences can be removed by first digesting the A2 clone with EcoRI or PstI and Sau3A (or any appropriate pair of enzymes that both remove the MAO-A insert from the clone and digest it into fragments). The digested MAO-A-encoding DNA is then subcloned into EcoRI or (PstI) and BamHI digested pBR322, and the subcloned fragments are then screened with radioactive human DNA. Subclones containing repetitive DNA will hybridize strongly and these will be excluded; the negative subclones will be rescreened with the HM11 clone and the postives from this screen will be retained and used as the RFLP probe. The RFLP procedure can be performed as described in Drayna et al., 1986, Biotechniques 4: 412 and Watkins et al., 1988, Biotechniques 6: 310.

RNase -A Cleavage Assay

MAO-A gene alterations such as deletions, insertions, rearrangements and, in addition, point mutations, which cannot be detected by Southern blotting, may be detected by Ribonuclease A (RNase A) cleavage at mismatched base pairs in MAO-A RNA:DNA or RNA:RNA duplexes. Human skin fibroblasts and lymphocytes can be used, respectively, as sources for MAO-A and MAO-B RNAs. The RNase A cleavage assay is based on the fact that some mismatch sites in RNA hybrids with RNA or DNA will be cleaved by RNase A. A single RNA probe can be used to identify the presence of a base substitution, or pair of overlapping probes can be used to unambiguously locate mutation sites. The precise requirements for susceptibility to RNase A attack are not yet clear, but it seems likely that 30–50% of possible single base mispairings will be cleaved. Mismatches resulting from deletions, insertions, or rearrangements offer greater potential for RNase A cleavage because of more extensive single-stranded regions within the hybrids. The RNase A cleavage assay (described in detail in Gibbs et al., 1987, Science 236: 303) can be performed using a radioactively labeled restriction fragment containing the human MAO-A gene from the HM11 MAO-A cDNA or a labeled antisense RNA synthesized from that DNA, as follows.

The antisense RNA can be synthesized by first inserting the MAO-A restriction fragment into the pSP6 vector and transcribing RNA from the sense strand. The DNA is removed by treatment with DNase. The radio-labeled MAO-A probe is hybridized to poly-(A)+RNA isolated according to conventional methods (Maniatis et al., supra). The hybrids are then treated with RNase A to digest single-stranded regions and internal mismatch sites, and the resulting fragments analysed by denaturing polyacrylamide gel electrophoresis and autoradiography. Further modification of the RNase A assay can be found in Winter et al., 1985, Proc. Nat. Aca. Sci. 82: 7575, and Myers et al, 1985, Science 230: 242.

Sequencing of Genomic DNA

The MAO-A cDNA sequence can also be used to scan for mutations in the coding region of MAO-A. First, the DNA polymerase chain reaction (PCR) of Saiki et al. (1985, Science 230:1350) and as further modified by Lee et al. (1988, Science 239: 1288) will be used to enzymatically amplify MAO-A coding sequences from enomic DNA, using oligonucleotide sequences from Hm11 as primers. One primer must be complementary to the (−) strand and the other to the (+) strand of the MAO-A gene. Second, the amplified DNA will be sequences by the dideoxy method (Sawyer, 1977 PNAS 74:5463; Read et al, 1986, Biotechniques 4:306). Once the sequence at the mutations site in MAO-A is determined, a synthetic oligonucleotide spanning the mutation site is then synthesized and used as a probe for routine screening of similar mutations by selective hybridization to genomic blots.

Restriction Site Probes

If the mutated sequence lies within a restriction enzyme recognition site, then the sample DNA can be screened for the mutation as follows. The MAO-A mutation, present in genomic DNA or cellular RNA, is first amplified by hybridizing the DNA or RNA to synthetic oligonucleotide primers whose sequences are specific only for the MAO-A sequence. A radioactively labeled synthetic oligonucleotide probe, or a DNA fragment, complementary to the wild type MAO-A gene is then hybridized to the amplified DNA. The probe sequence is selected so as to span the genetic mutation. A second reference restriction enzyme cleavage site also lies within the probe sequence but does not contain the genetic mutation. When the probe forms a hybrid with the wild type DNA, the two respective enzyme cleavaqe sites will be digested by their respective enzymes, and fragments will be produced that are visible on a polyacrylamide or agarose gel. However, when the probe forms a hybrid with the mutant DNA, the hybrid will contain a mismatch and the restriction site containing the mismatch will not be cleavage by the restriction enzyme; only the reference site will be cleavable. Thus, the restriction fragments produced from digestion of the mutant hybrids will form a different visual pattern on a gel from that found using wild type hybrids.

RNA Blot Analysis

An MAO-A DNA or RNA probe can also be used to detect abnormal MAO-A gene expression using a Northern blot, as described by Maniatis et al., supra, to identify the RNA encoding MAO-A. (The MAO-B RNA can also be detected with the MAO-A RNA probe using this technique provided the hybridization temperature or salt concentration are adjusted.) MAO-A gene abnormalities, e.g., regulatory mutations or gene rearrangements, can be detected by comparing amounts of MAO-A-specific RNA in abnormal and normal samples or by detecting an altered transcript size.

Assay for MAO Inhibition. The MAO-A polypeptide, expressed and purified as described above, can be used to test compounds as MAO inhibitors potentially useful in the treatment of certain psychotic disorders. These compounds can be added to the sample under conditions permitting a reaction involving MAO-promoted catalysis of the oxidative deamination of amines; this method is described by Edelstein and Breakefield, 1986, Cell. Mol. Neurobiol. 6: 121.

Assay for MAO. MAO-A can also be used diagnostically by making monoclonal antibodies made from the MAO-A protein or protein fragments to assess altered MAO enzyme levels associated with human diseases. Monoclonal antibodies capable of detecting MAO-A and MAO-B, or MAO-A alone, can be prepared according to conventional procedures, as described in Kohler and Milstein, 1976, Euro. J. Immunol. 6: 511. The monoclonal antibody can be used in a conventional ELISA to detect and quantitate MAO enzyme levels in human tissue samples, e.g., blood cells or skin cells. An unusually high or low level of MAO could be indicative of a genetic disorder involving the MAO genes, and also of certain MAO-associated diseases.

Therapeutic Administration of MAO-A. The MAO-A polypeptide can be used locally, e.g., in the stomach, to catalyze the deamination of monoamines released from foods; so-called "false transmittors". Patients who are treated with MAO inhibitors have abnormally low levels of MAO activity and are therefore not able to deaminate monoamines while under treatment; the result is an increased sensitivity to foods containing monoamines.

MAO-A can be administered, to patients requiring MAO-A, contained in capsules which are acid-resistant, orally or by intravenous injection in amounts ranging 0.1-5 mg/kg body weight.

The MAO-A gene or the recombinant MAO-A polypeptide can be used to treat MAO-deficient individuals, for example, manic depressives or individuals suffering from Norrie's disease, which in some cases is characterized by a total absence of both the MAO-A and MAO-B genes. A cDNA clone for human MAO-A has been used to establish the deletion of its corresponding gene in two male cousins with Norrie disease. No MAO-A activity was detected in their fibroblasts. MAO-B activity in platelets and fibroblasts from these patients was also nondetectable. Moreover, major catecholamine metabolites, including vanillylmandelic acid (VMA), homovanillic acid (HVA and 3-methoxy-4-hydroxyphenylglycol (MHPG), were reduced substantially in their urine. These findings indicate that gene(s) necessary for MAO-A and MAO-B activities are deleted in these patients. This genetic deletion is believed to be in the Xp11.3 region of the X chromosome. Recombinant human MAO-A polypeptide can be administered to patients such as these who are deficient in MAO-A. Alternatively, the human MAO-A gene can be used in gene therapy as a source of MAO-A. In order to effect a lasting reversal of the metabolic defects which cause diseases associated with MAO-A deficiencies, gene sequences must be introduced in an expressible form into cells which have an extensive capacity to proliferate and regenerate tissue.

Gene Transfer

Gene transfer into live animals requires methods to transform very large numbers of cells efficiently. Techniques for DNA-mediated gene transfer are useful for experiments in cultured cells, but are inadequate for experiments in primary cells cultures or live animals. Therefore, highly efficient methods have been developed in which recombinant genes are packaged into engineered virus particles and introduced into cells by infection with the recombinant virus; this technique is termed viral-mediated gene transfer, and the recombinant viruses are termed viral vectors. In certain cases, it might be advantageous to express a transferred gene only in certain tissues or to regulate the level of expression of the gene. An expression vector can be designed using a promoter that functions in all cells or only in select cells, e.g., simian viral 40 or adenoviral promoters direct high level transcription in virtually all cells. Some promoters inherently direct expression in a tissue-specific manner. Promoters from hemoglobin genes will direct transcription only in certain bone marrow derived cells, while promoters from the neurofilament, tyrosine hydroxylase, or glialfibrillary acidic protein (GFAP) genes will direct transcription only in certain cells of the nervous system. Other promoters are active only in the presence of various hormones or drugs. The use of such promoters in expression vectors allows transcription of the recombinant gene to be regulated in vivo. As a means of therapy for MAO-A deficient patients, cultured cells which have been infected with viruses containing the MAO-A gene, can be transplanted into desired target regions.

Deposits

*E. coli* cells containing HM11 and A2 have been deposited with the American Type Culture Collection, Rockville, Md., on June 30, 1988, and assigned ATCC Accession Numbers 67740 and 67741, under the terms of the Budapest Treaty. Applicants assignees acknowledge their responsibility to replace these cultures should they die before the end of the term of a patent issued hereon, and their responsibility to notify the ATCC of the issuance of such a patent, at which time the deposits will be made irrevocably available to the public for at least thirty years after the date of deposit or five years after the last request or the enforceable life of the patent, whichever is longer. Until that time the deposits will be made available to the Commissioner of Patents under the terms of 37 CFR §1.14 and 35 USC §112.

Other embodiments are within the following claims.

We claim:

1. A recombinant DNA molecule encoding human monoamine oxidase type A.

2. The DNA molecule of claim 1, said DNA molecule comprising the sequence of genomic DNA encoding MAO-A.

3. The DNA molecule of claim 1, said DNA molecule comprising the sequence of cDNA encoding MAO-A.

4. A vector comprising DNA encoding human monoamine oxidase type A.

5. The vector of claim 4, comprising the following elements operably linked, 5' to 3: promoter, DNA encoding signal peptide sequence, and DNA encoding human MAO-A.

6. A cell transformed with the vector of claim 5.

7. The cell of claim 6, said cell being a bacterial cell.

8. The cell of claim 6, said cell being a mammalian cell.

9. The cell of claim 6, said cell being a yeast cell.

10. A method of producing recombinant human MAO-A, said method comprising
    providing the cell of claim 7, 8, or 9
    culturing said cell in culture medium, and
    isolating said recombinant human MAO-A from said cultured cell or said medium.

11. A bacterial cell transformed with the vector of claim 4, A.T.C.C. accession number 67740.

12. A bacterial cell transformed with the vector of claim 4, A.T.C.C. accession number 67741.

* * * * *